United States Patent [19]

Kitajima et al.

[11] 3,951,851

[45] Apr. 20, 1976

[54] PROCESS OF PRODUCING ASPIRIN-CONTAINING CAPSULES

[75] Inventors: Masao Kitajima; Asaji Kondo; Fuminori Arai, all of Asaka, Japan

[73] Assignee: Fuji Photo Film Co., Ltd., Minami-ashigara, Japan

[22] Filed: May 29, 1973

[21] Appl. No.: 364,478

[30] Foreign Application Priority Data

May 29, 1972 Japan.............................. 47-53088

[52] U.S. Cl................................. 252/316; 424/35
[51] Int. Cl.²...................................... B01J 13/02
[58] Field of Search...................... 252/316; 424/35

[56] References Cited
UNITED STATES PATENTS 3,242,051  3/1966  Hiestand et al................. 252/316 X
3,645,911  2/1972  Van Besauw et al.............. 252/316
3,691,090  9/1972  Kitajima et al.................. 252/316

*Primary Examiner*—Richard D. Lovering
*Attorney, Agent, or Firm*—Sughrue, Rothwell, Mion, Zinn and Macpeak

[57]  ABSTRACT

Process of producing aspirin-containing capsules which comprises (1) dispersing aspirin particles in a solution of a cellulose derivative in an organic solvent partially miscible with water; (2) adding the dispersion to an encapsulation medium comprising water containing organic solvent(s) partially miscible with water with or without aspirin; (3) stirring the mixture to form a fine dispersion of the aspirin; and (4) evaporating off the organic solvent to deposit the cellulose derivative around the aspirin particles.

11 Claims, No Drawings

PROCESS OF PRODUCING ASPIRIN-CONTAINING CAPSULES

BACKGROUND OF THE INVENTION

1. Field of the Invention

The present invention relates to a process for the encapsulation of aspirin with a cellulose derivative. More particularly, the invention relates to a process of encapsulating aspirin in which water containing an organic solvent partially miscible with water and/or a small amount of aspirin is used as the encapsulation medium.

2. Description of the Prior Art

Processes of producing cellulose capsules containing aspirin are known. For example, there is known a method utilizing the phase separation of ethyl cellulose and polyethylene by heating and cooling it in a pure organic solvent such as cyclohexane. Such a method is accompanied by the danger caused by the requirement to heat cyclohexane to temperatures near its boiling point during phase separation, and the necessity for a complicated operation of separating polyethylene by filtration.

There is also known a process of producing such capsules utilizing the phase separation of a concentrated aqueous salt solution and acetone. However, in this process salt adhered to the walls of the capsules formed must be washed away with water, an additional troublesome operation.

These are, accordingly, technical problems which should be solved in encapsulation techniques for aspirin.

SUMMARY OF THE INVENTION

Accordingly, one object of the present invention is to provide a process for easily and efficiently producing aspirin-containing capsules in an aqueous medium which is not accompanied by the above-mentioned defects of the prior art.

DETAILED DESCRIPTION OF THE INVENTION

The above-mentioned object of the present invention can be attained by the excellent process of this invention, details of which will be described below:

1. As the capsule wall-forming substance, a cellulose derivative such as an alkyl cellulose, preferably ethyl cellulose, most preferably having an ethoxyl content of from 40.8 to 49.5%, is used. The term "cellulose derivative" means cellulose in which a hydrogen atom of at least one hydroxyl group of the cellulose molecule has a substituent.

2. A solution of the cellulose derivative is prepared by dissolving it in an organic solvent which is a solvent for the cellulose derivative and is properly miscible with water (at least about 1 wt%, i.e., for 100 grams of water at least 1 gram of the solvent mixes with water; the maximum preferred degree of miscibility is about 35 g per 100 grams of water). Then, aspirin particles are dispersed in the solution to form a dispersion. In this case, aspirin can be dissolved in the solution of the cellulose derivative, but it is preferred to choose an organic solvent that dissolves a low amount of aspirin. The cellulose derivative is completely dissolved by the organic solvent. The resulting solution contains the cellulose derivative of from about 1 to 10% by weight (i.e., concentration of the solution).

3. As the encapsulation medium, water having dissolved therein about 1 wt% to the almost saturated amount (see Table 1) of an organic solvent partially miscible with water (which may be same or different from the solvent(s) of step(2)), water having dissolved therein at least about 0.01 wt% aspirin, or water containing the organic solvent and aspirin as described above is prepared. While the maximum amount of aspirin is not overly important, the maximum amount of aspirin dissolved in 100 g of water at 20°C is about 0.6 g. It is thus seen the variation is relatively small.

4. The aspirin-containing dispersion prepared in step (2) is added to the aforesaid encapsulation medium maintained at any desired temperature not over 25°C, preferably at a temperature of not over 18°C, but above the freezing point thereof, and the mixture is stirred to divide the aspirin-containing dispersion into the particles of a size of about 0.1 to about 2 mm. By evaporating off the organic solvent while stirring, the cellulose derivative is deposited around aspirin particles as walls, whereby a great number of capsules containing aspirin are prepared simultaneously. The process is conveniently completed in about 1 to about 4 hours. The pressure used is preferably somewhat lower than atmospheric pressure, e.g., about 750 to about 500 mmHg. Excessively low pressures should be avoided as this may make a hole in the capsule-wall. The solvent can be evaporated off, e.g., by stirring the solution containing the solvent, in addition, by blowing air thereagainst. It is preferred to employ a solvent having a boiling point of no greater than 100°C which is readily volatile.

The solvents which are used in the present invention are those which scarcely dissolve aspirin (at most, several percent, which is negligible for manufacturing capsules). Further, though it is natural that a few percent of the aspirin is dissolved by the polymer solution and/or water (encapsulation medium) at the equilibrium state (concentration), this is also negligible for manufacturing capsules.

It should also be noted that the form and size of the capsules can be effectively adjusted by previously adding or saturating solvent(s) for the cellulose derivative(s) used in the present invention in water, since a rapid diffusion of the solvent from the cellulose derivative-containing solution to water is thereby prevented when the solution is incorporated in water.

According to the present invention, although the reason for this is unclear, the cellulose derivative is used so effectively as the capsule walls that neither solid beads nor crumbs of the cellulose derivative are formed.

In addition, by the process of this invention capsules having a most preferred size, i.e., from about 0.2 to about 1 mm, can be obtained by controlling stirring and also a stable product of constant quality can be obtained. Moreover, aspirin-containing capsules encapsulated by the cellulose derivative having long durability can be obtained since aspirin is not dissolved out of capsules and the evaporation of the organic solvent can be smoothly conducted during the encapsulation.

The decomposition of aspirin into salicylic acid is hardly observed.

After completing encapsulation, the capsules are recovered from the aqueous medium by filtration and the remaining solvent can easily be removed from the capsules by a blast of warm air or by vacuum drying. The recovered encapsulation medium can be repeatedly used merely by supplementing fresh organic solvent.

The materials which can be employed in the present invention will now be explained in further detail.

It is desirable to use aspirin having a particle size of about 50 to about 500 microns as listed on Japanese Pharmacopoeia. As the cellulose derivative, ethyl cellulose having an ethylation degree of about 47 to about 50%, which is commercially available under the tradename "N-100" from Hercules Co., Ltd., is convenient for practical use, but the cellulose derivative is not necessarily limited thereto and persons skilled in the art can select various kinds of cellulose derivatives.

Typical organic solvents partially miscible with water include alcohols, ethers, ketones, esters, etc., which are exemplified in Table 1 below. From the viewpoint of the dissolving of the cellulose derivatives (especially ethyl cellulose) and aspirin, ease of evaporation, cost, ease of recovery, etc., esters or mixtures of the solvents described above are preferred.

Table 1

| Solvent | Boiling Point (°C) | Amount Dissolved in 100 g of water (Temperature in °C in parentheses) |
|---|---|---|
| (Alcohols) | | |
| Isobutanol | 104 | 9(20) |
| sec-Butanol | 99 | 22(20) |
| Amyl Alcohol | 130 | 2.6(20) |
| (Ethers) | | |
| Ethyl Ether | 34 | 10(10) |
| (Ketones) | | |
| Methyl Ethyl Ketone | 80 | 26(22) |
| (Esters) | | |
| Ethyl Formate | 54 | 10(18) |
| Methyl Acetate | 57 | 33(22) |
| Ethyl Acetate | 77 | 9(15) |
| Propyl Acetate | 101 | 1.9(20) |
| Isopropyl Acetate | 90 | 3.2(20) |

The amount of the cellulose derivative employed as the wall substance of the aspirin-containing capsules can be freely selected in the range of about 1/5 to about 1/100 (by weight) of the aspirin to be dispersed in the organic solvent(s), but is preferaby about 1/20 to about 1/50 the weight of the aspirin. The solution in which aspirin is dispersed is preferably used in a concentration of about 1 to about 10 wt% of the cellulose derivative.

The amount of the encapsulation medium used can be about 3 to 19 times the amount of aspirin dispersed in the organic solvent, but the amount is preferably about 5 to 7 times from the viewpoint of ease of preparation and economy.

Having thus generally described the invention, the following examples are offered to illustrate preferred embodiments of the invention.

EXAMPLE 1

Into a solution of 1.5 g of ethyl cellulose N-100 (tradename) in 35 ml of ethyl acetate were dispersed 28.5 g of aspirin particles of about 300μ to about 50μ in particle size. The dispersion thus obtained was added to 200 ml of aspirin-saturated water as an encapsulation medium while maintaining all components at 15°C, and the mixture was stirred to form small droplets of 300 to 500μ [aspirin: cellulose ratio about 1:19]. By continuing the stirring, ethyl acetate was evaporated off over about 1 hour at atmospheric pressure to provide 30 g of ethyl cellulose-encapsulated aspirin. 95 wt% of the total aspirin particles were encapsulated in walls about 1 to ca. 2μ thick, as commonly the process provides walls of ca. 1–3 μ thick containing about 10 – 30 times the capsule weight of aspirin.

1 g of the thus obtained aspirin-containing capsules was incorporated in 1 liter of artificial gastric juice at 37°C and the time required for dissolving one half of the total weight of the encapsulated aspirin was measured. The time was found to be 60 minutes. On the other hand, the time required for dissolving the same total amount of aspirin which was not encapsulated was about 15 minutes.

EXAMPLE 2

Aspirin-containing capsules were obtained as in Example 1 except that a solution of 2 g of aspirin and about 20 ml of ethyl acetate in 200 g of water was used as the encapsulation medium.

While the invention has been described in detail and with reference to specific embodiments thereof, it will be apparent to one skilled in the art that various changes and modifications can be made therein without departing from the spirit and scope thereof.

What is claimed is:

1. A process of producing aspirin containing microcapsules which comprises:
   1. dispersing aspirin particles in a solution of a cellulose derivative in an organic solvent partially miscible with water;
   2. adding the dispersion to an encapsulation medium comprising (A) water and an organic solvent partially miscible with water or (B) water, an organic solvent partially miscible with water and aspirin, the amount of organic solvent present in the encapsulation medium being at least about 1 weight percent and the amount of the aspirin if present in the encapsulation medium being at least about 0.01 weight percent;
   3. stirring the mixture to form a fine dispersion of the aspirin;
   4. evaporating off the organic solvent to thereby encapsulate the aspirin particles in the cellulose derivative.

2. A process as claimed in claim 1 wherein the cellulose derivative is an alkyl cellulose.

3. A process as claimed in claim 2 wherein the cellulose derivative is ethyl cellulose.

4. A process as claimed in claim 1 wherein the organic solvent of step (1) is at least about 1 weight % miscible with water and up to about 35 weight % miscible with water.

5. A process as claimed in claim 4 where the cellulose derivative in step (1) is completely dissolved by the organic solvent, the solution of step (1) containing the cellulose derivative in an amount of from about 1 to about 10% by weight.

6. A process as claimed in claim 1 wherein the amount of organic solvent partially miscible with water in the encapsulation medium is less than the saturated amount of the organic solvent.

7. A process as claimed in claim 6 wherein the amount of the cellulose derivative is in the range of about 1/5 to about 1/100 (by weight) of the aspirin dispersed in the organic solvent(s).

8. A process as claimed in claim 7 where the amount of the encapsulation medium is from about 3 to about 19 times the amount of aspirin dispersed in the organic solvent.

9. A process as claimed in claim 8 where the encapsulation medium is maintained at a temperature not over 25°C but above the freezing point thereof while stirring to drive off the solvent.

10. The process of claim 1 wherein the encapsulation medium comprises water and an organic solvent partially miscible with water.

11. The process of claim 1 wherein the encapsulation medium comprises water and an organic solvent partially miscible with water and aspirin.

* * * * *